US012257093B2

(12) United States Patent
Panchagnula et al.

(10) Patent No.: US 12,257,093 B2
(45) Date of Patent: Mar. 25, 2025

(54) WALK-IN LAB TEST FOR LUNG MORPHOMETRY CHARACTERIZATION

(71) Applicants: Indian Institute of Technology Madras, Chennai (IN); Sri Venkateswara Institute of Medical Sciences (SVIMS), Tirupati (IN)

(72) Inventors: Mahesh V Panchagnula, Chennai (IN); Karthiga Devi S G, Chennai (IN); Mohan Alladi, Tirupati (IN)

(73) Assignees: Indian Institute of Technology Madras, Chennai (IN); Sri Venkateswara Institute of Medical Sciences (SVIMS), Tirupati (IN)

( * ) Notice: Subject to any disclaimer, the term of this patent is extended or adjusted under 35 U.S.C. 154(b) by 406 days.

(21) Appl. No.: 17/769,333

(22) PCT Filed: Oct. 13, 2020

(86) PCT No.: PCT/IN2020/050879
§ 371 (c)(1),
(2) Date: Apr. 14, 2022

(87) PCT Pub. No.: WO2021/074923
PCT Pub. Date: Apr. 22, 2021

(65) Prior Publication Data
US 2022/0354366 A1 Nov. 10, 2022

(30) Foreign Application Priority Data
Oct. 15, 2019 (IN) .............................. 201941041658

(51) Int. Cl.
*A61B 6/50* (2024.01)
*A61B 5/00* (2006.01)
(Continued)

(52) U.S. Cl.
CPC ................ *A61B 6/50* (2013.01); *A61B 5/004* (2013.01); *A61B 6/481* (2013.01); *A61B 6/5217* (2013.01);
(Continued)

(58) Field of Classification Search
CPC . G06T 2207/30061; G06T 7/12; G06T 7/136; A61B 6/50; A61B 5/08
See application file for complete search history.

(56) References Cited

U.S. PATENT DOCUMENTS

2009/0285763 A1 11/2009 Finlay et al.

FOREIGN PATENT DOCUMENTS

| CA | 2622987 C | * | 2/2018 | ............. A61K 38/21 |
| EP | 1011423 A1 | | 6/2000 | |

OTHER PUBLICATIONS

C. Wang, "Chapter 2: Morphometry of the human respiratory system", Interface Science and Technology, vol. 5, pp. 7-30, 2005 (Year: 2005).*

(Continued)

*Primary Examiner* — Joel Lamprecht
*Assistant Examiner* — Nyrobi Celestine
(74) *Attorney, Agent, or Firm* — Harita S Achanta

(57) ABSTRACT

The present invention relates to a method for estimating lung morphometry based on aerosol deposition characteristics using an imaging means such as a gamma camera to scan the lungs. An adaptive image threshold technique is used to determine the ratio of deposition in central to peripheral region of the lung (C/P ratio). The morphometric parameters such as length and diameter of distal lung airways ($P_8$ and $P_9$ respectively) and mean alveolar diameter ($d_{alv}$) are determined from aerosol retention data and clearance data.

6 Claims, 5 Drawing Sheets

(51) Int. Cl.
*A61B 6/00* (2024.01)
*G06T 7/00* (2017.01)
*G06T 7/136* (2017.01)

(52) U.S. Cl.
CPC ............ *G06T 7/0012* (2013.01); *G06T 7/136* (2017.01); *G06T 2207/30061* (2013.01)

(56) References Cited

OTHER PUBLICATIONS

J. Fleming et al, "The Use of Combined Single Photon Emission Computed Tomography and X-ray Computed Tomography to Assess the Fate of Inhaled Aerosol", Journal of Aerosol Medicine and Pulmonary Drug Delivery, vol. 24, No. 1, pp. 49-60, 2011 (Year: 2011).*

J. Fleming et al, "Determination of regional lung air volume distribution at mid-tidal breathing from computed tomography: a retrospective study of normal variability and reproducibility", BMC Medical Imaging, vol. 14, No. 25, pp. 1-14, 2014 (Year: 2014).*

V. Galindo-Filho et al, "Radioaerosol Pulmonary Deposition Using Mesh and Jet Nebulizers During Noninvasive Ventilation in Healthy Subjects", Respiratory Care, vol. 60, No. 9, pp. 1238-1246, Sep. 2015 (Year: 2015).*

S. Devi et al, "Designing aerosol size distribution to minimize inter-subject variability of alveolar deposition", Journal of Aerosol Science, vol. 101, pp. 144-155, 2016 (Year: 2016).*

C. Holsbeke et al, "Use of functional respiratory imaging to characterize the effect of inhalation profile and particle size on lung deposition of inhaled . . . agonists delivered via a pressurized metered-dose inhaler", Therapeutic Advances in Respiratory Disease, vol. 12, p. 1-15, 2018 (Year: 2018).*

G. Taylor et al, "Gamma scintigraphic pulmonary deposition study of glycopyrronium/ formoterol metered dose inhaler formulated using co-suspension delivery technology", European Journal of Pharmaceutical Sciences, vol. 111, pp. 450-457, 2018 (Year: 2018).*

J. Virchow et al, "Lung Deposition of the Dry Powder Fixed Combination Beclometasone Dipropionate Plus Formoterol Fumarate Using NEXThaler Device in Healthy Subjects, Asthmatic Patients, and COPD Patients", Journal of Aerosol Medicine and Pulmonary Drug Delivery, vol. 31, No. 5, pp. 269-280, 2018 (Year: 2018).*

Am J Physiol Lung Cell Mol Physiol., Jun. 15, 2013, 304(12):L831-43.

J Aerosol Med., Summer 2007;20(2):127-40.

Sci Rep. Mar. 28, 2018;8(1):5341.

* cited by examiner

WALK-IN LAB TEST FOR LUNG MORPHOMETRY CHARACTERIZATION

CROSS-REFERENCE TO RELATED APPLICATIONS

The present application is a continuation of an International Application Number PCT/IN2020/050879, with a filing date of Oct. 13, 2020, the entire disclosure of which is incorporated herein by reference for all purposes. The present application claims the benefit of foreign priority application number IN201941041658, with a filing date of Oct. 15, 2019, the entire disclosure of which is incorporated herein by reference for all purposes.

FIELD OF THE INVENTION

The present invention relates to a method for the estimation of lung morphometry through aerosol deposition measurements through the use of gamma scintigraphy scan and adaptive image threshold technique.

BACKGROUND OF THE INVENTION

The lung is one of the internal vital organs, which is constantly exposed to the external environment. This is the underlying cause of several respiratory infections. However, it is also well known that certain people are more prone to infections while others are not. According to World Health Organization (WHO), out of the top 10 causes of global deaths, the deaths caused by chronic obstructive pulmonary disease (COPD), lower respiratory infections and cancers of trachea, bronchus and lung occupy $3^{rd}$, $4^{th}$ and $6^{th}$ positions respectively.

Personalized medicine is an emerging field due to the fact that 'one size does not fit all'. The challenges for personalization in pulmonary therapeutics are daunting and therefore still remain unaddressed. Though respiratory diseases impose an immense worldwide health burden, the diagnostic tests used to detect the early occurrence of respiratory diseases are insensitive to the patient symptoms and disease. For example, in the case of diseases such as asthma or COPD, the treatment is advocated based on measurements of lung function data obtained from spirometry which does not give any information about the regional deposition happening inside the lung. This leads to the prescribed medications not being effectively delivered to essential sites of infection. Current focus of research in personalized medicine being creation of patient specific prototype models with the aid of imaging tools, and the creation and analysis of such a model is extremely cumbersome. Such a model is possible only from CT derived data and also for initial few generations of the lung only. It is difficult to obtain the dimensions of smaller airways at the distal end using current imaging tools and techniques. Existing technologies are also expensive due to the need to build customized models for each individual based on identification of specific markers that could segregate the regional deposition of a given dose of aerosol. In this scenario, more sensitive markers for accurate detection and treatment of respiratory diseases are a compelling need of the decade.

Inhalation is the commonly sought route for administration of drugs to treat various respiratory diseases, and also the most viable route for respirable pathogens to enter and trigger infection of any kind. The deposition of a drug in lung is considered to be a measure of local bioavailability thus serving to be a surrogate to identify clinical response of inhaled drugs. When it comes to the dosage of drug at the essential site, inter-subject variability in drug deposition plays a major role. The minor morphometric changes of the lung from generation 5 till the end, causes variability in alveolar deposition. Thus, essentially the changes in morphological features of the lung could explain inter-subject variability in deposition. The prediction of human lung morphometry for any given individual would be clinically relevant while personalizing the treatment. There are no studies which report the realistic lung morphometry for a given individual. Thus, prediction of length and diameter of each generation of the respiratory tract and the alveolar diameter through deposition measurement would do a great benefit to the medical practitioners, so that the dose could be engineered to the needs of the individual.

EP1011423A1 discloses a non-invasive process for the analysis of an internal element in a body of a human or animal. The process comprises of the steps: providing a contrast agent to the patient in any suitable form, such as neat liquid, aerosol, vapor, or emulsion; receiving scanned data reflective of a portion of a human or animal body in a processor; and processing the scanned data in the processor into three-dimensional volume and functional data based on the mathematical model representative of the internal body element. The abnormality of the airways is determined based on the comparison between the scanned data and the baseline data. It is possible to assess diseases down to approximately the $12^{th}$ through $17^{th}$ generation bronchi which are about 1 mm diameter in the adult.

US20090285763A1 discloses a delivery system and a method for the delivery of an aerosol drug to an infant. It comprises a diagnostic module configured to provide geometrical properties of the nasal airway of the infant as the output. A computer program is used to determine the aerosol drug dose based on the said geometrical properties of the nasal airway. The required geometrical information is obtained by a suitable method such as CT, Cone Beam Computed Tomography, X-ray, fluoroscopy, ultrasound, PET, or gamma scintigraphy.

Counter W B et al. of McMaster University published an article titled 'Airway and pulmonary vascular measurements using contrast-enhanced micro-CT in rodents' discloses a method to visualize both the pulmonary airways and vasculature of the Sprague-Dawley rat and BALB/c mouse in situ using contrast-enhanced micro-CT imaging. From these images, parameters such as diameter, length, and branching angles were automatically measured to create an anatomical database for normal rodent lungs. Contrast agent was infused in the airways using a perfusion pump. Images for rats were reconstructed using a Feldkamp filtered back-projection algorithm. In the rat lung, an average of 562 airways was segmented. Their diameters ranged from 0.23 to 2 mm over 20 generations.

Tossici-Bolt et al. of Southampton University Hospital NHS Trust, University of Southampton and Cyber Medicine published articles (Analytical technique to recover the third dimension in planar imaging of inhaled aerosols: (1) Impact on spatial quantification, and (2) Estimation of the deposition per airway generation). The articles disclose methods to recover 3D information from theoretically generated planar images. The results obtained from their technique were compared in terms of conducting and bronchial airway deposition fraction obtained from SPECT study. It was concluded that the approximate estimates of 3D airway distribution parameters can be derived from planar imaging. However, the errors are significantly higher than with SPECT.

Belchi et al. of University of Southampton published an article titled 'Lung Topology Characteristics in patients with Chronic Obstructive Pulmonary Disease' which discloses an analytical tool based on persistent homology that extracts quantitative features from chest CT scans to describe the geometric structure of the airways inside the lungs. It is claimed that the new radiomic features stratify COPD patients in agreement with the GOLD guidelines for COPD and can distinguish between inspiratory and expiratory scans. It also claimed that the results of the study are a proof of concept that topological methods can enhance the standard methodology to create a finer classification of COPD and increase the possibilities of more personalized treatment.

However, these prior art studies fail to specifically address the morphology differences among individuals that bring about the inter-subject variability in deposition. For accurate customized drug dosage, it is essential to have a cost-effective technique that would also be capable of providing lung morphometry of even the last generation of lung airways. In addition, the prior art does not disclose any method to quantify the deep lung dimensions, especially those associated with the bronchioles from the $17^{th}$ to $23^{rd}$ generations.

The present invention provides a method which would in future evolve into a walk-in lab test, wherein patients get their lung map through an imaging means such as a conventional gamma scan. This test can identify and quantify features in the distal end of the lung which is the most important part of the lung from a functional point of view that is difficult to be imaged using existing imaging techniques.

Object of the Invention

The principal object of the present invention is to develop a walk-in lab test for estimating the lung morphometry for determination of length and diameter of distal lung airways, mean alveolar diameter and lung boundary based on aerosol deposition characteristics.

SUMMARY OF THE INVENTION

The present invention provides a method for measuring lung morphometry using adaptive image threshold technique. The method of the present invention comprises radio-aerosol deposition in a subject, and capturing a series of lung images using an imaging means post-inhalation of said radio-aerosol from t=0 to upto t=24 hours. Said adaptive image threshold technique is applied to the obtained images for determining the ratio of the deposition of said radio-aerosol in the central region to the deposition of said radio-aerosol to the peripheral region of lung (C/P ratio) for identifying lung boundary. The parameters of the lung morphometry including the length ($P_8$) and diameter ($P_9$), and mean alveolar diameter ($d_{alv}$) of the $17^{th}$ generation lung airway to the $23^{rd}$ generation lung airway are measured using said radio-aerosol deposition and clearance data comprising the time, volume, or percentage of said radio-aerosol in the central region and the peripheral region of the lungs. Said adaptive image threshold technique comprises using automated iterative procedures for drawing a Region of Interest (ROI) on the images of the lung, for determining a Central region (C) of said ROI, and determining a Peripheral region (P) of said ROI, to determine the ratio of radio-aerosol deposition in the Central region to the radio-aerosol deposition in the Peripheral region (C/P) of the lung based on the characteristics of said radio-aerosol deposition in said Central region and said Peripheral region, thereby determining the lung morphometry. Said adaptive image threshold technique comprises of converting images obtained from imaging at t=0 hours and upto t=24 hours post-inhalation of the radio-aerosol to gray scale images; cropping said gray scale images to make the right lung as the only focus and obtaining uniform dimensions of said gray scale images for all the subjects; calculating the lung boundary of the image by extracting the boundaries of the lung outline at a given threshold through an automated iterative procedure until a threshold value for obtaining maximum lung boundary is achieved; obtaining the area of the right lung by superimposing lung boundary over the first image obtained immediately post-inhalation of radio-aerosol; calculating the C/P ratio from the ratio of the area of the central region to the area of the peripheral region based on the image intensities in the central region (C) and the peripheral region (P); and shrinking right lung area to create an C/P ratio using an iterative procedure, wherein said iterative procedure comprises calculating and recalculating the boundaries of said central region and peripheral region based on the threshold values and image intensities until the central region is shrunk to one-third of the right lung boundary. Said adaptive image threshold technique is used for determining the parameters of the lung morphometry based on said C/P ratio through an optimization procedure comprising minimizing an error function.

BRIEF DESCRIPTION OF THE DRAWINGS

The summary of the present invention, as well as the detailed description, are better understood when read in conjunction with the accompanying drawings that illustrate one or more possible embodiments of the present invention, of which:

FIG. 3A illustrates the diameter of the airway predicted at every generation for the sample subjects using the proposed method;

FIG. 3B illustrates the length of the airway predicted at every generation for the sample subjects using the proposed method;

DETAILED DESCRIPTION OF THE INVENTION

Figure 1:
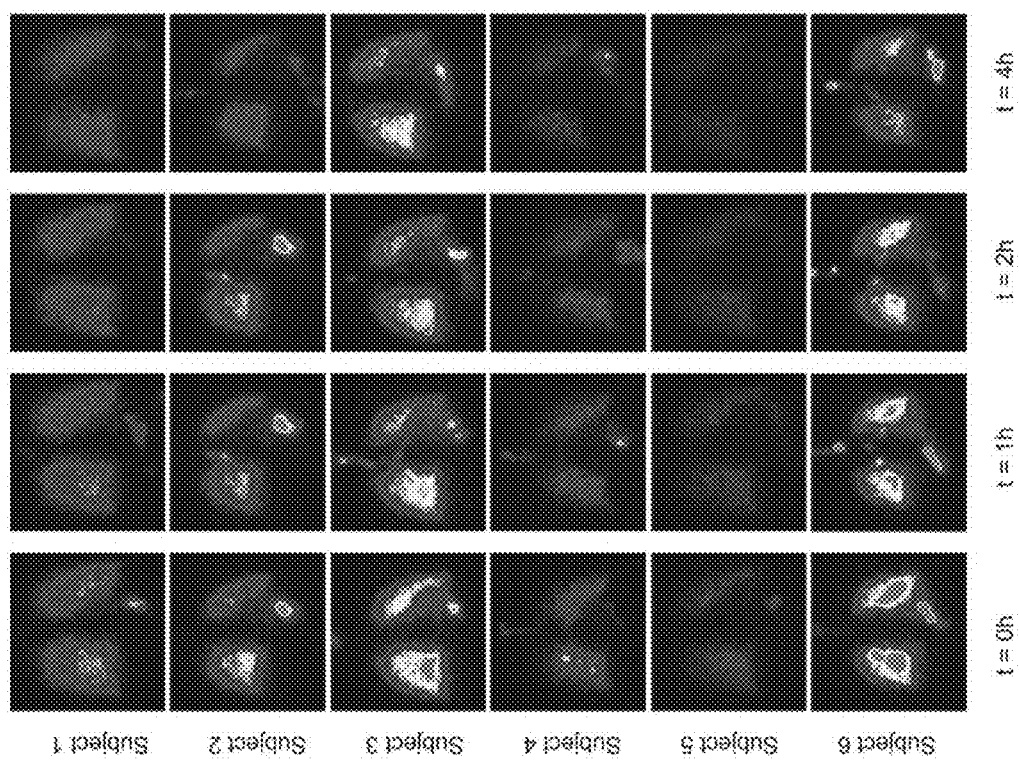
FIG. 1 illustrates the images obtained using gamma camera at time intervals of 0, 1, 2, and 4 hours.

The present invention is related to a method for estimating lung morphometry including the length and diameter of distal lung airways, mean alveolar diameter and lung boundary based on the aerosol deposition characteristics obtained by an imaging means. According to the embodiments of the present invention, the imaging means may be for example, a gamma camera. According to the present invention, adaptive image threshold technique is applied for the estimation of the lung morphometry.

According to an embodiment of the present invention, the proposed method can create a morphology map as well as any required regional deposition map for any given subject.

According to an embodiment of the present invention, the radio-aerosol used for measuring deposition characteristics includes but is not limited to 99mTechnetium phytate radio-aerosol generated using a Biodex® Venti-scan® radio-aerosol delivery system.

According to an embodiment of the present invention, the camera used for acquiring lung images includes but is not limited to gamma camera.

The radio-aerosol is delivered to the lungs using any oral or nasal compliance. As an exemplary case in the present invention, a radio-aerosol such as 99mTechnetium phytate generated using a Biodex® Venti-scan® radio-aerosol delivery system is given to the subject through a mouth piece. The nose is clamped and the subject is instructed to breathe through their mouth. The radio-aerosol solution contains 20 mCi of radioactivity. The subject inhales the aerosol for about three minutes so that about 2 mCi, i.e., one-tenth of the total preparation is deposited inside the thorax.

An imaging means such as gamma scintigraphy is used to acquire lung images at time intervals (t) of 0, 4 and 22 hours. In the subsequent analysis, only the first image post-inhalation is used for extracting the C/P ratio in which case the original test dosage of the radio-aerosol could be further reduced.

The C/P ratio is defined as the ratio of deposition in the central to peripheral region of the lung. It responds to changes in important factors that influence the deposition characteristics in the lung such as particle size, inhaled airflow rate, and airway patency. The peripheral zone comprises mostly of small airways and alveoli. The central zone consists of larger central airways. Said characteristics of said radio-aerosol deposition include retention data and clearance data of aerosol in lungs, wherein said retention data and clearance data of said radio-aerosol in lungs include the time, volume or percentage of said radio-aerosol in the lungs.

The conventional method of obtaining the C/P ratio is to draw a region of interest (ROI) on the right lung to demarcate the central (C) and peripheral (P) regions of the lung. The time activity curves are obtained for each of the two regions. After correcting the counts for decay and background, the central to periphery ratio of counts C/P is obtained from the initial image, post-inhalation of the radio-aerosol. There are various methods available in the literature to draw these regions of interest. One of the methods is intended to find the C/P ratio of which the central region is one-third of the lung area and the remaining two-third region is considered as the peripheral lung region. The present invention implements the adaptive image threshold method for the calculation of C/P ratio, and estimation of the lung morphometry.

In order to find the lung area, the first image is recorded at t=0 hour. It is important to minimize user induced variability in drawing the region of interest (ROI) based on which the central to peripheral ratio is calculated. In the present invention, an adaptive image threshold technique in MATLAB® was used for finding the lung outline to draw the region of interest (ROI). Thus, the C/P ratio found using this technique is free of inter-subject variability in drawing ROI manually. The gray scale level or the image threshold in MATLAB® is automated for the subjects based on the intensity of the pixels in the image to provide the lung outline. In each subject, there is a particular threshold value which gives the maximum lung area. Increasing the image threshold above this value decreases the lung area drastically. All the other intensity threshold values below this particular threshold yield a lower lung area. This particular threshold value helps detect all the connected components of the image giving rise to the maximum lung area. The adaptive technique is used to effectively identify the lung boundary.

According to the embodiments of the present invention, the morphometric parameters for an individual subject are determined from the aerosol deposition and clearance data. The morphometric parameters considered in accordance with the present invention include length ($P_8$) and diameter ($P_9$) of the last generations, i.e., the $17^{th}$ generation airway to the $23^{rd}$ generation airway, and the mean alveolar diameter ($d_{alv}$). These three parameters determine the airway morphometry in the distal lung.

In order to identify the morphometric parameters, an error function ($\varepsilon$) is postulated as a normed difference between the numerical predictions of $(C/P)_m$ ratio and experimentally determined values C/P ratio, specifically, $\varepsilon = |C/P - (C/P)_m|$. The numerical predictions of $(C/P)_m$ are derived using the model proposed by Devi et al (Designing aerosol size distribution to minimize inter-subject variability of alveolar deposition, *Journal of Aerosol Science,* 2016). The parameters $P_8$, $P_9$, and $d_{alv}$ are determined by minimizing this error. The proposed method which uses C/P ratio is robust, convergent and predicts physically relevant values for the parameters. The total lung capacity of each subject is used as constraint in the minimization process. The corresponding lengths and diameters of the bronchioles at various generations are calculated using these parameters and Weibel's morphometry.

According to the various embodiments of the present invention, the method for estimating lung morphometry comprises delivering radio-aerosol in a subject, generating a plurality of images of the lung of said subject post-inhalation of the radio-aerosol using an imaging means, wherein said images are obtained from imaging at t=0 hours and upto t=24 hours post-inhalation of said radio-aerosol, applying an adaptive image threshold technique to draw a Region of Interest (ROI) on said images of the lung for determining ratio of said radio-aerosol deposition in the Central region (C) to said radio-aerosol deposition in the Peripheral region (P) of the lung (C/P ratio), and determining the parameters of lung morphometry based on said C/P ratio through an optimization procedure comprising minimizing an error function. Said adaptive image threshold technique comprises (i) converting said images obtained from imaging at t=0 hours and upto t=24 hours post-inhalation of said radio-aerosol to gray scale images; (ii) cropping said gray scale images to make the right lung as the only focus and obtain uniform dimensions of said gray scale images for all the subjects; (iii) calculating the lung boundary of said image obtained post-inhalation of said radio-aerosol by extracting the boundaries of the lung outline at a given threshold through an automated iterative procedure until a threshold value for obtaining maximum lung boundary is achieved; iv) obtaining the area of the right lung by superimposing said lung boundary over the first image obtained immediately after the inhalation of said radio-aerosol; (v) calculating the C/P ratio from the ratio of the area of the central region to the area of the peripheral region; and shrinking said right lung area to create an area ratio obtained in step (v) using an iterative procedure.

In the adaptive image threshold technique of the present invention, said ratio of the area of the central region to the area of the peripheral region is obtained through an iterative procedure, wherein said iterative procedure includes calculating and recalculating the boundaries of said central region and peripheral region based on the threshold values and image intensities until the central region is shrunk to one-third of the right lung boundary.

While certain preferred embodiments and examples are disclosed herein, it is to be understood that these embodiments and examples are only illustrative, and the inventive subject matter is not limited to the specifically disclosed embodiments. Rather, the scope of the invention extends to other alternative embodiments, uses, modifications, and equivalents thereof.

EXAMPLES

Study Design and Participants:

In this study, six healthy, non-smoking individuals with pulmonary function tests within the normal range and no respiratory illness were selected. In all the cases, a detailed history was considered and a thorough physical examination was carried out especially focusing on the respiratory system. In all the subjects, a chest radiograph (postero-anterior view) was also taken to ascertain normal lung structure. Lung volumes were determined using spirometry. The anthropometric and spirometry data of the subjects under study are listed in Table 1.

TABLE 1

Anthropometric and spirometry data

| Subject | Age (yr) | Height (cm) | Weight (kg) | FEV1 (L) | FEV1 % Predicted | FEV1/FVC | FEV1/FVC % Predicted |
|---|---|---|---|---|---|---|---|
| 1 | 26 | 175 | 75 | 4.43 | 119 | 0.89 | 106 |
| 2 | 38 | 175 | 86 | 3.45 | 102 | 0.91 | 111 |
| 3 | 25 | 172 | 81 | 3.78 | 102 | 0.87 | 95 |
| 4 | 39 | 173 | 66 | 3.32 | 101 | 0.81 | 99 |
| 5 | 24 | 182 | 87 | 4.47 | 108 | 0.88 | 98 |
| 6 | 41 | 159 | 65 | 2.68 | 110 | 0.91 | 108 |

FEV1-Forced expiratory volume in one second;
FVC-Forced Vital Capacity

In the gamma scintigraphy study, the 99mTechnetium phytate radio-aerosol was generated using a Biodex® Venti-scan® radio-aerosol delivery system. The mass median aerodynamic diameter (MMAD) of aerosol produced by the nebulizer is 0.5 μm.

Aerosol Administration and Image Acquisition:

The subjects were made to sit comfortably in a chair and relax for 10 minutes. Then 99mTechnetium phytate radio-aerosol generated using a Biodex® Venti-scan® radio-aerosol delivery system was given through a mouth piece. The nose was clamped and the subjects were instructed to breathe through their mouth. The radio-aerosol solution used on all subjects contained 20 mCi of radioactivity. The subjects inhaled the aerosol for about three minutes so that about 2 mCi, i.e. one-tenth of total preparation was deposited inside the thorax. As an exemplary case, the procedure followed by Guleria et al, was followed in acquiring the images at t=0 hour, 4 hours and 22 hours. In the subsequent analysis, only the first image for extracting the C/P ratio was considered. Hence, the original test dosage of the radio-aerosol could be further reduced.

FIG. 1 of the present invention illustrates the images obtained using a gamma camera at intervals (t) of 0, 1, 2, 4 hours. The red and yellow-coloured bright spots indicate that more aerosol has been retained in those regions. The bright spots in the stomach are due to the assimilation of the aerosol at the mouth walls. The trend of clearance kinetics can be observed from the reducing intensity at increasing time intervals. However, each image is unique for every subject and identifies the importance of inter-subject variability even among a small cohort of healthy subjects. Comparing the initial image of subject 5 with subject 3 or subject 6, it appears as though subject 5 had inhaled about $\frac{1}{4}^{th}$ of aerosol compared to subject 3 and subject 6. Thus, this study has attempted to bring out the morphometric cause of this variation. The huge variation in brightness is a striking feature which emphasizes the need for personalized treatment.

Determination of C/P Ratio:

According to the embodiments of the present invention, in order to find the lung area, the first image was recorded initially at t=0 hour, i.e., immediately after inhalation. It is important to minimize user induced variability in drawing the ROI based on which the central to peripheral ratio is calculated.

The procedure to draw ROI using adaptive threshold technique comprises of:

i. converting the images obtained at t=0, and at t=2 hours post-inhalation, to gray scale images;

ii. cropping said images to make the right lung as the only focus and obtain uniform dimensions of said gray scale images for all the subjects;

iii. calculating the lung boundary of said image obtained post-inhalation of said radio-aerosol by extracting the boundaries of the lung outline at a given threshold through an automated iterative procedure until a threshold value for obtaining maximum lung boundary is achieved;

iv. obtaining the right lung area by superimposing said lung boundary over the first image obtained immediately after the inhalation of said radio-aerosol;

v. calculating the C/P ratio from the ratio of the area of the central region to the area of the peripheral region, wherein said area ratio is based on the image intensities in the central region and the peripheral region; and vi. shrinking said right lung area to create an area ratio obtained in step (v) using an iterative procedure, wherein said iterative procedure comprises calculating and recalculating the boundaries of said central region and peripheral region based on the threshold values and image intensities until the central region is shrunk to one-third of the right lung boundary.

In accordance with some of the embodiments of the present invention, the area ratio between the central and peripheral regions is 0.33. The ratio of the total pixels in both the regions corresponds to the C/P ratio.

Figure 2:
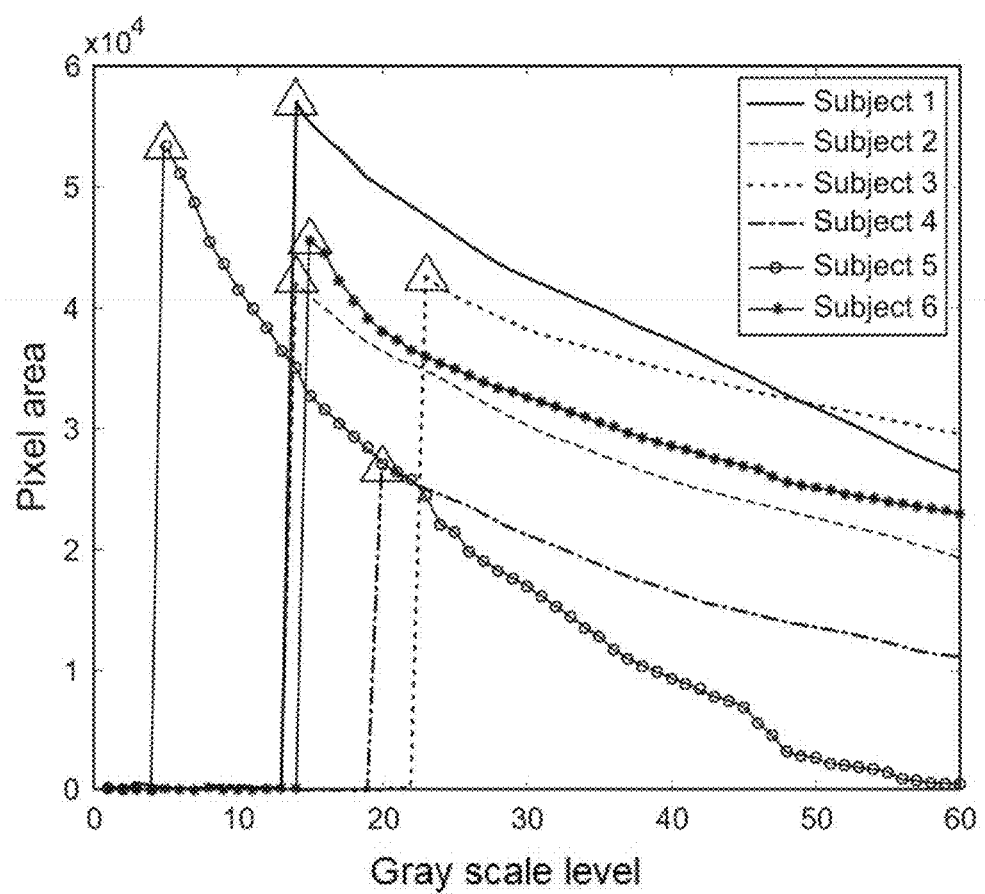
FIG. 2 illustrates the plot of gray scale level and pixel area for the subjects under study.
Figure 3A:
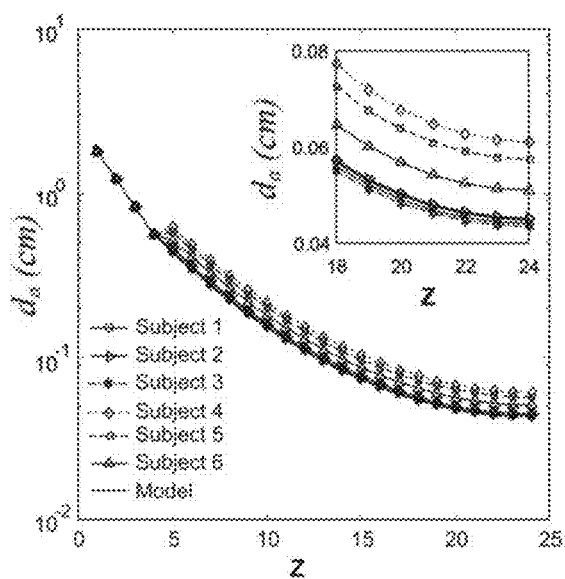
FIG. 3A and FIG. 3B illustrate the morphology features of the human lung.
Figure 3B:
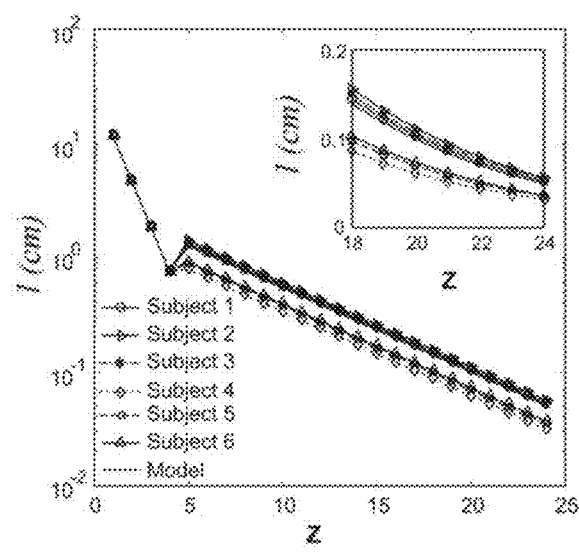
Figure 4:
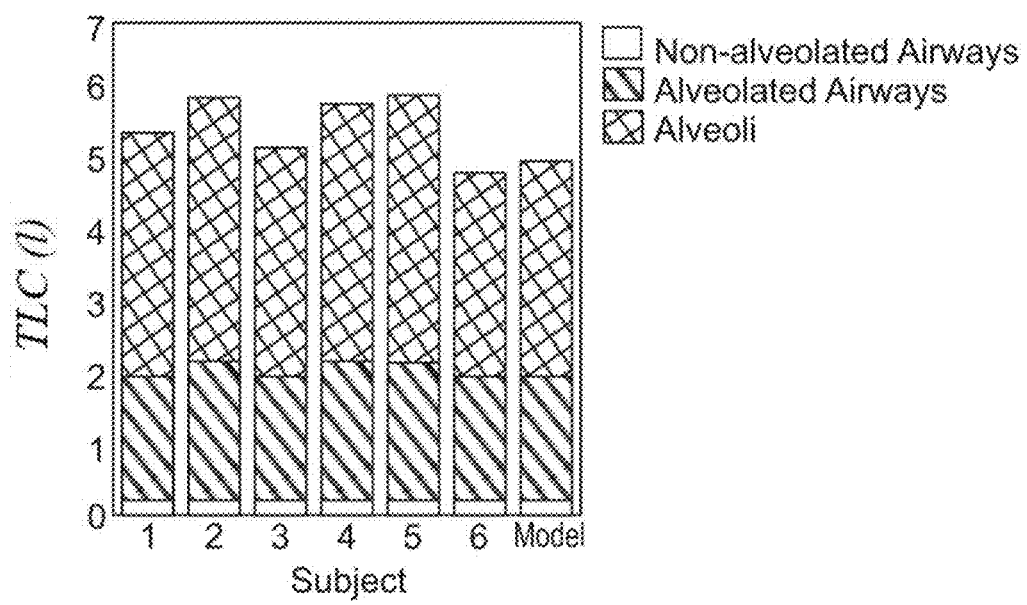
FIG. 4 illustrates the TLC predicted for generations 0<z<17 and 17<z<23 for sample subjects.
Figure 5:
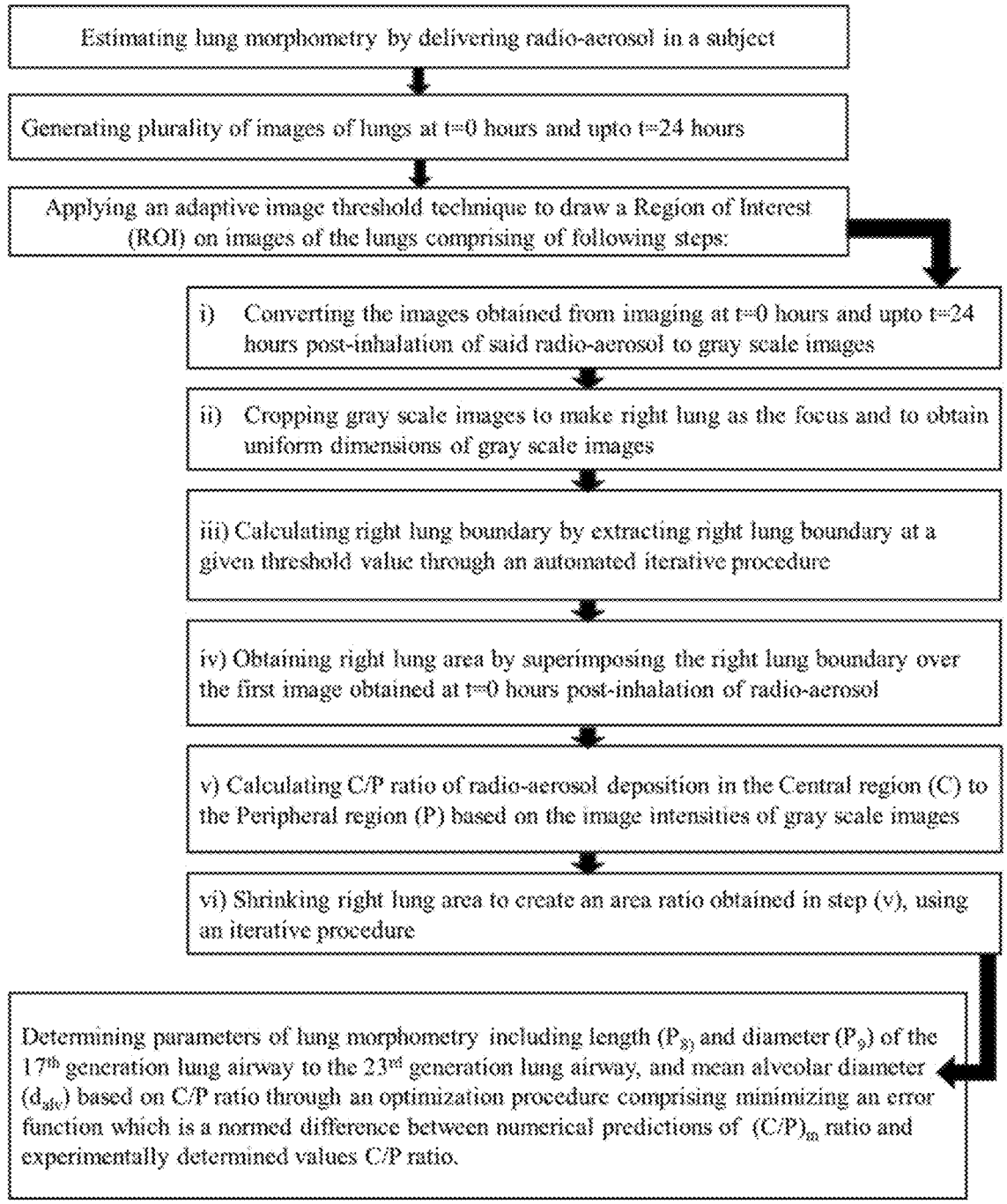
FIG. 5 illustrates the Flow chart/protocol for the Walk-in lab test.

Using the above method, the total number of pixels versus the gray scale level for each of the subjects is shown in FIG. 2. This figure is part of the intelligent threshold technique proposed for finding the C/P ratio. The gray scale level indicates the value of the pixel intensity in an image. The number of pixels in the y-axis of the figure corresponds to the right lung area. The line styles are varied to indicate subjects 1 to 6. The value marked with a triangle marker in the figure shows the maximum right lung area and its corresponding threshold. The lung outline determined from the first image is superimposed over the same image post-inhalation and the total lung area is determined using image processing in MATLAB. This area is also divided into two regions-one-third representing the central region and two-thirds representing the peripheral region.

Determination of Subject-Specific Morphometric Markers:

In accordance with the embodiments of the present invention, the morphometric parameters for an individual subject are identified from the aerosol deposition and clearance data. From the present invention, three parameters, $P_8$, $P_9$, and $d_{alv}$ have been identified as important lung morphometry markers.

In order to identify the morphometric parameters, the error function ($\varepsilon$) was employed. The parameters obtained using said approach are tabulated in Table 2. Table 2 shows the predicted parameters as well as their deviation from the Weibel values (in percentage terms). The corresponding lengths and diameters of the bronchioles at various generations calculated using these parameters and Weibel's morphometry model are also graphically depicted in FIG. 3A and FIG. 3B.

TABLE 2

Parameters predicted C/P ratios in accordance with present invention

| | Predicted Parameters | | | Deviation from Weibel Values | | |
|---|---|---|---|---|---|---|
| Subject | $P_8$ | $P_9$ | $d_{alv}$ | $P_8$ | $P_9$ | $d_{alv}$ |
| 1 | 2.59 | 1.33 | 0.0281 | 4 | 2 | 4 |
| 2 | 2.80 | 1.33 | 0.0289 | 12 | 2 | 6 |
| 3 | 2.69 | 1.28 | 0.0279 | 8 | −2 | 2 |
| 4 | 1.56 | 1.79 | 0.0286 | −38 | 38 | 5 |
| 5 | 1.70 | 1.69 | 0.0290 | −30 | 30 | 6 |
| 6 | 1.84 | 1.50 | 0.0269 | −6 | 15 | −1 |

FIG. 3A and FIG. 3B depict the variation of bronchiole diameters and lengths at each generation in a sample size of six subjects. The average diameters and lengths of a model individual are also plotted in the same figure for reference. The numerical approach predicts that subjects 4 and 5 have larger diameter bronchioles but are shorter in length. In contrast, subjects 2 and 3 have smaller diameter bronchioles but are longer. This information is corroborated with corresponding images presented in FIG. 1. It is observed that subjects 2 and 3 have greater aerosol deposition, while subjects 4 and 5 have lower aerosol deposition. The increased wall surface area due to longer bronchioles appears to be a self-consistent explanation of this observation. The insets in FIG. 3A and FIG. 3B show the lengths and diameters of the alveolated airways only. Even though the parameters $P_8$ and $P_9$ vary about ±30% from the Weibel values for subjects 4 and 5 (Table 2), the lengths and diameters are physically consistent for all the six subjects. Table 2 also presents the deviation of other functional aspects of the lung.

TABLE 3

Change in surface area and lung volumes in relation to Weibel values

| Subject | % Change in predicted surface area | % Change in predicted airway volume | % Change in predicted alveolar volume |
|---|---|---|---|
| 1 | 6 | 8 | 11 |
| 2 | −3 | 17 | 20 |
| 3 | 4 | 4 | 5 |
| 4 | 6 | 18 | 16 |
| 5 | −8 | 17 | 21 |
| 6 | −6 | −2 | −3 |

Total Lung Capacity (TLC) is another physiologically relevant parameter. FIG. 4 shows the predicted TLC for the six subjects using the proposed method. The generations 0<z<17 represent the non-alveolated airways and the generations 17<z<23 represent the alveolated airways. It can be observed that the non-alveolated airway volume (0<z<17) remains almost the same for all subjects, while the alveolated airway volume (17<z<23) shows significant subject-to-subject variability in contributing to the total lung capacity. Therefore, variation in alveolar volume is a prime cause of inter-subject variability in TLC, and therefore aerosol deposition. The parameter $d_{alv}$ which is a measure of the mean alveolar diameter, shows only about 1% to 6% variation for all the subjects considered for the study (Table 2) and the corresponding alveolar volume varies by up to 21% (Table 3). This suggests that aerosol deposition is sufficiently sensitive to alveolar volume. The morphometric parameters associated with the later generations (17<z<23), which are immeasurable by current imaging modalities are well-predicted by the said approach of the present invention.

Table 3 shows the deviation of lung surface areas and total lung volumes for each subject from an average individual to indicate inter-subject variability. Lung surface area is an important factor influencing drug deposition. According to the embodiments of the present invention, the change in surface area for subject 5 amounts to about 8%. As the surface area for subject 5 is reduced by 8%, the drug absorption would also be reduced in this subject compared to an average individual. The percentage change in alveolar volumes for each subject is considerably greater than the volume changes of the airway passages.

According to the embodiments of the present invention, the alveolar volume, while being only about one-third of the total lung capacity, is a primary cause of inter-subject variation in morphometry. As the lung surface area and alveolar volume are fundamentally important parameters in drug delivery and absorption, it is important to estimate these parameters for an individual subject. Therefore, predicting the parameters would help the physician in personalizing the dosage and therapy of the patient. FIG. 5 represents the flow chart to indicate the protocol for the Walk-in lab test of the present invention. The protocol comprises prescription of a lung morphology test by the physician to an individual or subject, gamma scintigraphy test getting performed by the subject, obtaining $P_8$, $P_9$, and $d_{alv}$ in accordance with the embodiments of the present invention, obtaining a deposition map for the subject for any given size and distribution of the drug which is in the form of an aerosol, and prescription of appropriate customized drug dosage to the subject by the physician.

According to a preferred embodiment, the method for estimating lung morphometry comprises delivering radio-aerosol in a subject, generating a plurality of images of the lung of said subject post-inhalation of the radio-aerosol using an imaging means wherein said images are obtained from imaging at t=0 hours and upto t=24 hours post-inhalation of said radio-aerosol, applying an adaptive image threshold technique to draw a Region of Interest (ROI) on said images of the lung for determining the ratio of said radio-aerosol deposition in the Central region (C) to said radio-aerosol deposition in the Peripheral region of the lung (C/P ratio), and determining the parameters of the lung morphometry based on said C/P ratio through an optimization procedure comprising minimizing an error function. An error function was postulated as normed difference between the numerical predictions of C/P ratio and the experimentally measured values of the C/P ratios. The adaptive threshold technique comprises of converting the initial image obtained at t=0 hour post-inhalation and after upto twenty four hours post-inhalation of said radio-aerosol, to gray scale images; cropping said images to make the right lung as the only focus and obtain uniform dimensions for all the subjects; calculating the lung boundary of the image obtained post-inhalation of said radio-aerosol by extracting the boundaries of the lung outline at a given threshold through an automated iterative procedure until a threshold value for obtaining maximum lung boundary is achieved; obtaining the right lung area by superimposing the lung boundary over the first image obtained immediately after the inhalation of said radio-aerosol; calculating the C/P ratio from the ratio of the area of the central to the area of the peripheral region based on the image intensities in the central region and the peripheral region; and shrinking said right lung area to create said area ratio using an iterative procedure wherein the boundaries of said central and peripheral regions are calculated and recalculated based on the threshold values and image intensities until the central region is shrunk to one-third of the right lung boundary. Based on said C/P ratio, the parameters of the lung morphometry including the length ($P_8$) and diameter ($P_9$) of the $17^{th}$ generation lung airway to the $23^{rd}$ generation lung airway, and the mean alveolar diameter ($d_{alv}$) of said lung airways are determined through an optimization procedure comprising minimizing an error function.

It is to be understood, however, that the present invention would not be limited by any means to the techniques, and approaches that are not specifically described, and any change and modifications to the techniques and approaches can be made without departing from the spirit and scope described in the present invention.

We claim:

1. A method for estimating lung morphometry comprising of:
    delivering radio-aerosol in a subject;
    generating a plurality of images of lungs of said subject post-inhalation of the radio-aerosol using an imaging means,
        wherein said images are obtained from imaging at t=0 hours and upto t=24 hours post-inhalation of said radio-aerosol;
    applying an adaptive image threshold technique to draw a Region of Interest (ROI) on said images of the lungs for determining a Central region (C) of said ROI, and a Peripheral region (P) of said ROI, and determining ratio of radio-aerosol deposition in the Central region (C) to radio-aerosol deposition in the Peripheral region (P) of the lungs (C/P ratio) based on characteristics of said radio-aerosol deposition post-inhalation in the Central region (C) and the Peripheral region (P),
        wherein said adaptive image threshold technique comprises of:
        i) converting said images obtained from imaging at t=0 hours and upto t=24 hours post-inhalation of said radio-aerosol to gray scale images;
        ii) cropping said gray scale images to make right lung as the only focus and obtain uniform dimensions of said gray scale images for said subject;
        iii) calculating right lung boundary from said gray scale images by extracting said right lung boundary at a given threshold value through an automated iterative procedure until said threshold value for obtaining maximum said right lung boundary is achieved;
        iv) obtaining right lung area by superimposing said right lung boundary over first image obtained from imaging at t=0 hours post-inhalation of said radio-aerosol;
        (v) calculating the C/P ratio from the ratio of the area of the central region to the area of the peripheral region,
            wherein said ratio of the area of the central region to the area of the peripheral region is obtained based on image intensities of said gray scale images in the central region (C) and the peripheral region (P); and
        vi) shrinking said right lung area to create an area ratio obtained in step (v), using an iterative procedure,
            wherein said iterative procedure comprises calculating and recalculating boundaries of said central and said peripheral regions based on said threshold value and said image intensities of said gray scale images until the central region is shrunk to one-third of said right lung boundary; and
    determining parameters of lung morphometry based on said C/P ratio through an optimization procedure comprising minimizing an error function,
        wherein said parameters of lung morphometry include length ($P_8$) and diameter ($P_9$) of the $17^{th}$ generation lung airway to the $23^{rd}$ generation lung airway, and mean alveolar diameter ($d_{alv}$) of said lung airways.

2. The method for estimating lung morphometry according to claim 1, wherein said radio-aerosol is delivered to the lungs using any oral or nasal compliance.

3. The method for estimating lung morphometry according to claim 1, wherein the imaging means is selected from a gamma imaging camera, CT scan, SPECT, and PET scan.

4. The method for estimating lung morphometry according to claim 1, wherein the characteristics of said radio-aerosol deposition in said Central region (C) and said Peripheral region (P) include retention data and clearance data of radio-aerosol in the lungs.

5. The method for estimating lung morphometry according to claim 4, wherein said retention data and said clearance data of said radio-aerosol in the lungs include time, volume, or percentage of said radio-aerosol in the lungs.

6. The method for estimating lung morphometry according to claim 1, wherein said minimizing an error function is a normed difference between numerical predictions of (C/P) m ratio and experimentally determined values C/P ratio.

* * * * *